ized is a layered double hydroxide capable of delamination...

(12) United States Patent
Ikematsu et al.

(10) Patent No.: US 8,388,987 B2
(45) Date of Patent: Mar. 5, 2013

(54) LAYERED DOUBLE HYDROXIDES THAT DELAMINATE IN WATER, THEIR MANUFACTURING PROCESS AND USE

(75) Inventors: Daisaku Ikematsu, Osaka (JP); Takeshi Okumiya, Osaka (JP)

(73) Assignee: Tayca Corporation, Osaka (JP)

( * ) Notice: Subject to any disclaimer, the term of this patent is extended or adjusted under 35 U.S.C. 154(b) by 1193 days.

(21) Appl. No.: 11/722,425

(22) PCT Filed: Dec. 20, 2005

(86) PCT No.: PCT/JP2005/023329
§ 371 (c)(1),
(2), (4) Date: Jun. 21, 2007

(87) PCT Pub. No.: WO2006/068118
PCT Pub. Date: Jun. 29, 2006

(65) Prior Publication Data
US 2008/0021115 A1    Jan. 24, 2008

(30) Foreign Application Priority Data
Dec. 22, 2004    (JP) ................. 2004-370532

(51) Int. Cl.
*A61K 8/02*    (2006.01)
(52) U.S. Cl. ........................................ 424/401
(58) Field of Classification Search .............. 424/400
See application file for complete search history.

(56) References Cited

U.S. PATENT DOCUMENTS

| | | |
|---|---|---|
| 5,073,573 A | 12/1991 | Martin et al. |
| 5,399,329 A | 3/1995 | Schutz et al. |
| 5,507,980 A | 4/1996 | Kelkar et al. |
| 5,539,135 A | 7/1996 | Breuer et al. |
| 5,728,366 A * | 3/1998 | Martin et al. ............... 423/594.1 |
| 2004/0171735 A1 * | 9/2004 | Choy et al. .................... 524/500 |

FOREIGN PATENT DOCUMENTS

| | | |
|---|---|---|
| JP | 1-164432 A | 6/1989 |
| JP | 6-505954 A | 7/1994 |
| JP | 9-511211 A | 11/1997 |
| JP | 10-503465 | 3/1998 |
| JP | 2000-86245 | 3/2000 |
| JP | 2004-351452 | 12/2004 |
| WO | WO 96/05140 | 2/1996 |
| WO | WO 99/41196 * | 8/1999 |

OTHER PUBLICATIONS

International Search Report corresponding to PCT/JP20051023329, dated Mar. 28, 2006.
Yoshio; Composite of Laminar Multiple Hydroxide and Saccharide, Its Production, and Recovering Material for Saccharide; Patent Abstract of Japan; 10-279307; Oct. 20, 1998.

* cited by examiner

*Primary Examiner* — David J Blanchard
*Assistant Examiner* — Devang Thakor
(74) *Attorney, Agent, or Firm* — Millen, White, Zelano & Branigan, P.C.

(57) ABSTRACT

Disclosed is a layered double hydroxide capable of delamination in water comprising a plurality of basal layers of a double hydroxide of Formula:

$$M(II)_{1-x}M(III)_x(OH)_2$$

wherein M(II) is Mg, Zn or a combination thereof, M(III) is Al, and x is 0.2 to 0.33 and a plurality of intercalated layers between each adjacent basal layers of Mg acetate, Zn acetate or Ce acetate and water of intercalation. A process for producing the layered double hydroxide is also disclosed. The layered double hydroxide find use as an vehicle component or an anti-corrosive pigment of water-based protective coatings for metallic substrates, and as a humectant or a stabilizing agent for cosmetic preparations such as lotions, creams or foundations.

13 Claims, 5 Drawing Sheets

LAYERED DOUBLE HYDROXIDES THAT DELAMINATE IN WATER, THEIR MANUFACTURING PROCESS AND USE

TECHNICAL FIELD

The present invention relates to a layered double hydroxide that delaminates in water, its manufacturing process and use. The layered double hydroxide is capable of delamination due to intercalation layers of a multivalent metal acetate guest compound.

BACKGROUND OF THE INVENTION

Layered double hydroxides (LDH) are a class of layered compounds having anion exchangeability represented by the formula:

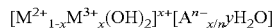

$$[M^{2+}_{1-x}M^{3+}_x(OH)_2]^{x+}[A^{n-}_{x/n} \cdot yH_2O]$$

Their crystal structure consists of a plurality of octahedral hydroxide layers (basal layers) in which a portion of bivalent metal ions is replaced with trivalent metal ions in the hydroxide, and a plurality of intercalation layers consisting of anions and water present between adjacent basal layers. The characteristic feature of LDH's resides in a wide variety of the species and ratios of metal ions of the basal layer and the combination of the basal layer and the intercalation layer. A large number of LDH's have been synthesized to date and their entrapment of various inorganic and organic anions has been studied.

The basal layers of LDH in general have a relatively high electrostatic charge density and, therefore, the electrostatic attraction force between the basal and intercalation layers are strong enough so that delamination could hardly occur like many clay minerals. Accordingly, only a few reports address an LDH capable of delamination in water. JP 2004-189671A discloses an LDH intercalated with an aromatic amino carboxylic acid such as p-aminobenzoic acid that delaminates in water or a lower alcohol such as ethanol to form a dispersion of delaminated LDH. It is explained that the delamination occurs as a result of enlarged spacing distance between the basal layers by the intercalated aminocarboxylic acid molecule having a larger molecular size than $CO_3^{2-}$ ion. However, the delamination of this LDH is complete in a good solvent of the aromatic aminocarboxylic acid such as p-aminobenzoic acid but not complete in water in which the aromatic aminocarboxylic acid is less soluble. A need exists for a new type of LDH that delaminates in water almost completely.

DISCLOSURE OF THE INVENTION

In one aspect, the present invention provides a layered double hydroxide capable of delamination in water comprising:

a plurality of basal layers of double hydroxide of Formula (I):

$$M(II)_{1-x}M(III)_x(OH)_2 \qquad (I)$$

wherein M(II) is Mg, Zn or a combination thereof, M(III) is Al, and x is 0.2 to 0.33, and a plurality of intercalation layers between each adjacent basal layers consisting of magnesium, zinc or cerium acetate and water of intercalation.

In another aspect, the present invention provides a process for producing the layered double hydroxide of the present invention. The process comprises the steps of calcining a carbonate-type layered double hydroxide of Formula (II):

$$[M(II)^{2+}_{1-x}M(III)^{3+}_x(OH)_2][(CO_3)_{x/2} \cdot yH_2O] \qquad (II)$$

wherein M(II), M(III) and x are as defined above, and y is a real number greater than zero;

reacting the calcined product with an aqueous solution of magnesium, zinc or cerium acetate;

separating the resulting solid product from the solution; and drying and pulverizing the separated solid product.

The starting carbonate LDH of Formula (II) in which M(II) is Mg is known as hydrotalcite.

The LDH of the present invention is capable of delamination in water to form a suspension or sol of delaminated particles. The resulting suspension exhibits significantly higher transmittance to visible light than the suspension of a non-delaminating LDH at the same concentration, indicating that the dispersion comprises delaminated microparticles of nanometer size. This dispersion or sol returns to the original LDH by drying. Accordingly, a transparent coating film may be formed on a metal substrate by applying the suspension or sol and then drying. The film may be converted to a scratch-resistant hard film by calcination at high temperatures. Consequently, a sol of the LDH of the present invention finds use as a anticorrosive coating composition for metallic substrates either alone or in combination with a known anticorrosive pigment, or as an auxiliary vehicle for improving the corrosion resistance of conventional water-based anticorrosive coating compositions.

The LDH of the present invention additionally finds use as a humectant or a stabilizing or thickening agent for cosmetic preparations, and as a flame retardant for plastics.

BEST MODE FOR CARRYING OUT THE INVENTION

Figure 1:
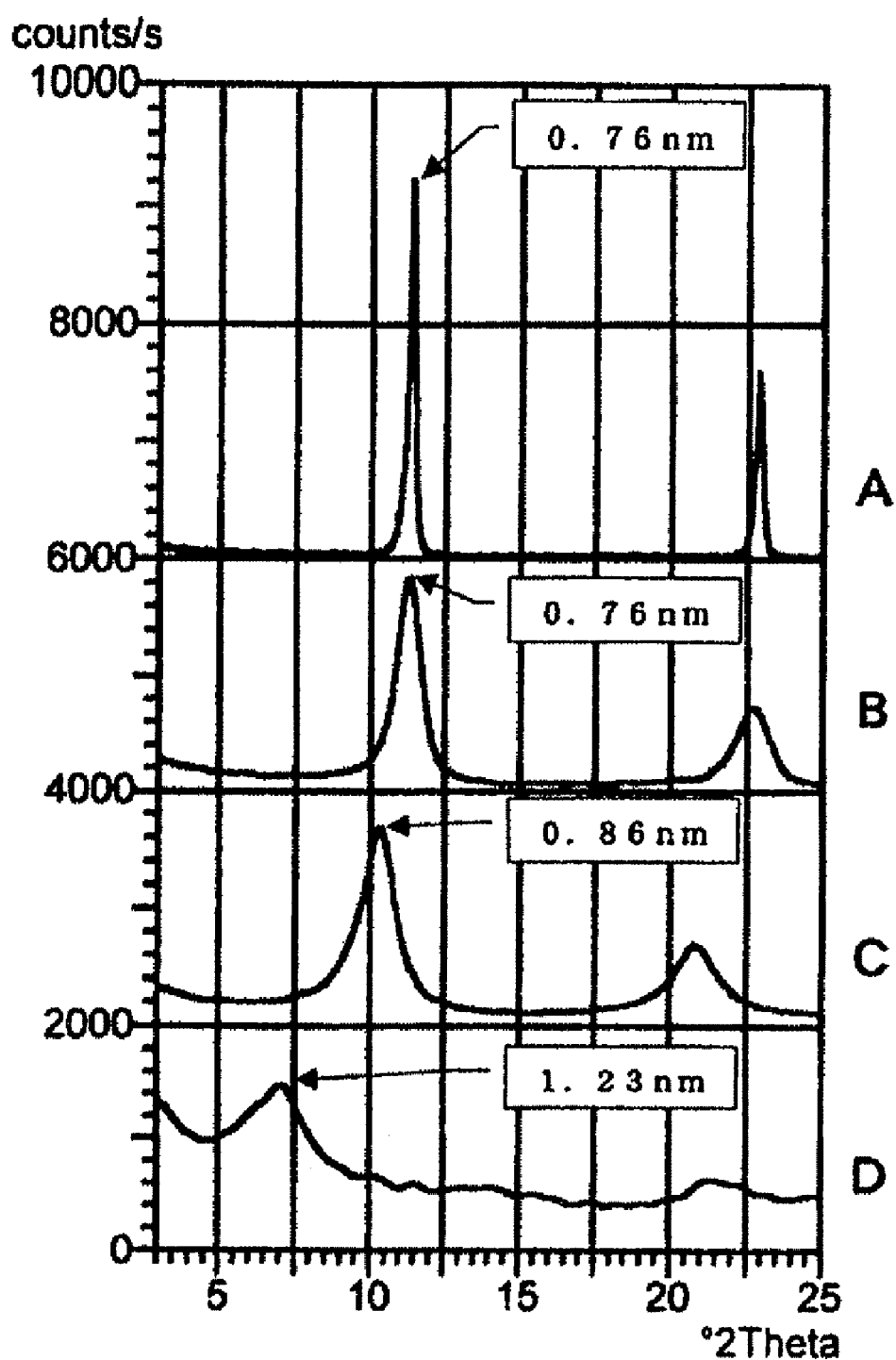
FIG. 1 shows the X-ray diffraction analysis of LDH of the present invention in comparison with the corresponding carbonate LDH and sodium acetate-intercalated LDH.

The LDH of the present invention may be produced from carbonate type LDH and a bivalent metal acetate to be intercalated by a process similar to the reconstitution method for producing the LDH intercalated with various anions. In the reconstitution method, a carbonate LDH is calcined at a temperature from 400° C. to 800° C. to remove major part of carbonate anions, and the calcined product is reacted with an aqueous solution of a guest anion to reconstitute LDH having the guest anion. In the present invention, the calcined carbonate LDH is reacted with an aqueous solution of magnesium, zinc or cerium acetate.

The starting carbonate LDH is represented by Formula (II):

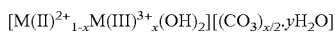

wherein M(II) is Mg, Zn or a combination thereof, M(III) is Al, and x is 0.2 to 0.33. The starting material is known as naturally occurring or synthetic hydrotalcite-like compounds. Some of synthetic hydrotalcite compounds are commercially available from Kyowa Chemical Industry Co., Ltd., Japan.

The calcined carbonate LDH may be reacted with an aqueous solution of the bivalent metal acetate at room temperature under stirring. The ratio of the bivalent acetate to the calcined carbonate LDH calculated as $Al_2O_3$ is preferably at least equimolar. The reaction product is usually obtained as a gel and may be separated from the reaction mixture by filtration or centrifugation before drying and pulverization into the LDH of the present invention in particulate form. When the X-ray diffraction pattern of the LDH of the present invention is compared with the X-ray diffraction patterns of carbonate LDH and sodium acetate-intercalated LDH respectively, the peak intensity is seen to be shifted toward lower angle side suggesting enlarged spacing between adjacent basal layers. When the FT-IR spectrum of the LDH of the present invention is compared with the FT-IR spectrum of sodium acetate-intercalated LDH, the characteristic absorption peak of carboxylate group is seen at around 1390-1430 $cm^{-1}$ which is different from the characteristic peak of the carboxylate group in the sodium acetate-intercalated LDH at around 1360-1390 $cm^{-1}$ suggesting that the binding mode of intercalated acetate salt is different between sodium acetate and the bivalent metal acetate although not fully elucidated.

Unlike the LDH intercalated with aromatic amino acid, the LDH of the present invention delaminates in water almost completely to form a viscous colloid solution or sol. The delamination is demonstrated by the X-ray diffraction analysis of the LDH when hydrating or swelling with different amounts of water. The peak intensity shifts toward lower angle side with increase in water and finally disappears. The shift of peak intensity indicates enlarged spacing between adjacent basal layers due to incorporation of water molecules finally resulting in destruction of crystalline structure. However, the destructed LDH returns upon drying to the original LDH which exhibits the same X-ray diffraction pattern before hydration. Thus the delamination occurs reversibly.

The suspension of delaminated LDH of the present invention exhibits significantly higher transmittance to visible light than the suspension of corresponding carbonate LDH at the same concentration. This is because the LDH delaminates into very fine particles of nanometer size.

By virtue of the foregoing properties, the LDH of the present invention finds use as a protective coating material for metallic substrates. The aqueous suspension of the inventive LDH (colloidal solution or sol) may be applied on the substrate and dried to form a continuous film and the drying. The dried film may be converted into a very hard, scratch-resistant transparent protective film by baking or calcining at a temperature above 350° C.

Alternatively, the LDH of the present invention may be formulated in water-based, metal-protective coating compositions as protective filler or pigment. It is known to incorporate a flaky filler or pigment such as mica, talc or kaoline so that a barrier layer against corrosive agents is formed by the orientation of flakes in the direction of major axis. Based on the same principle, the LDH of the present invention may be formulated in the coating composition for creating a barrier layer against corrosive agents. The LDH of the present invention has in its delaminated state a greater aspect ratio than the known flaky fillers and also a thickness of about 6-10 nm which is significantly smaller than the thickness of carbonate LDH of about 40-50 nm. The delaminated LDH of the present invention may undergo the orientation in the direction of major axis more easily to create the barrier layer compared to conventional flaky fillers and the carbonate LDH.

Vehicles used in conventional water-based coating compositions are well known in the art and include aqueous solutions, emulsions or dispersions of film-forming resins. Examples of the resins include alkyd resins, oil-free polyester resins, acrylic resins, epoxy resins, epoxy ester resins (epoxy acrylate resins), phenol resins, aminoplast resins, polyvinylidene chloride, polyurethane resins, chlorinate rubber, mixtures and modified resins thereof. The coating composition may be either air drying or thermosetting.

The water-based coating composition may comprises conventional anti-corrosive pigments. If used anti-corrosive pigments free of harmfull heavy metals such as lead or chromium are preferable. Examples thereof include phosphate pigments such as zinc phosphate, calcium phosphate or aluminum tri-polyphosphate;

molybdate pigments such as zinc molybdate; borate pigments such as zinc borate, calcium borate or barium metaborate; and calcium-substituted silica pigment.

Water-based metal protecting coating compositions are well known in the coating industry and further description will not be necessary.

The LDH of the present invention additionally finds use in the cosmetic industry as a humectant or a stabilizing thickener or a body pigment in the formulation of lotions, milks, creams or foundations.

EXAMPLES

The following examples are offered for illustrative purposes only. All parts and percentages therein are by weight unless otherwise indicated.

Part I. Preparation of LDH that Delaminates in Water

Example I-1

Mg—Al carbonate LDH available from Kyowa Chemical Industry Co., Ltd. under the name of DHT-6 was calcined at 700° C. for 20 hours. To 1 liter of 0.28 mol/L (60 g/L) solution of magnesium acetate tetrahydrate in water was added 96.3 g of the above calcined product. The mixture was stirred at room temperature for 15 hours and then filtered. The separated solid product (gel) was dried at 90° C. for 10 hours and then pulverized to give reconstituted LDH called LDH I-1.

Example I-2

Example I-1 was repeated except that the aqueous solution of magnesium acetate was replaced by 0.28 mol/L (94 g/L) solution of cerium acetate monohydrate to give reconstituted LDH called LDH I-2.

Example I-3

Example I-1 was repeated except that the aqueous solution of magnesium acetate was replaced by 0.28 mol/L (61.5 g/L) solution of zinc acetate dehydrate to give reconstituted LDH called LDH I-3.

Example I-4

To 2 liters of 1 mol/L aqueous solution of $Na_2CO_3$ were added dropwise 2.6 liters of 1 mol/L aqueous solution of ZnCl$_2$ and 1.4 liters of 1 mol/L aqueous solution of AlCl$_3$ while keeping the pH of the reaction mixture below 7. The mixture was kept at 40° C. for 1 hour. After removing chloride ions by repeated decantation, 2 liters of 1 mol/L solution of Na$_2$CO$_3$ was added to the reaction mixture and then refluxed for 5 hours. The resulting solid product was separated by filtration, washed with water, dried at 60° C. under reduced pressure for 24 hours, and pulverized to give Zn—Al carbonate LDH.

The LDH thus obtained was calcined at 450° C. for 20 hours. 115.1 g of the calcined product was added to 1 liter of 0.28 mol/L (61.5 g/L) solution of zinc acetate. Then the mixture was stirred at room temperature for 15 hours and evaporated to dryness at 100° C. to give LDH called LDH I-4.

Example I-5

Mg—Zn—Al carbonate LDH available from Kyowa Chemical Industry Co., Ltd. under the name of ALCAMIZER was calcined at 700° C. for 20 hours. 65.3 g of the calcined product was added to 1 liter of 0.1 mol/L (30.0 g/L) solution of magnesium acetate. The mixture was stirred at room temperature for 48 hours. The resulting solid product (gel) was separated by filtration, dried at 90° C. for 10 hours, and pulverized to give LDH called LDH I-5.

Comparative Example I-1

Example I-1 was repeated except that the aqueous solution of magnesium acetate was replaced by 0.28 mol/L (23 g/L) solution of sodium acetate to give reconstituted LDH called LDH I-6.

Part II. Characterization of LDH Produced in Part I

X-Ray Diffraction Analysis: Part 1

X-ray diffraction analysis was performed with respect to LDH I-1, I-2 and I-6 (for comparison) as well as commercially available Mg—Al-carbonated LDH (DHT-6 available from Kyowa Chemical Industry Co., Ltd.). The measurement was made using Nippon Philips X-ray diffractometer Model 1880 equipped with Cu tube at a voltage of 40 kV and a current of 30 mA. Scanning was carried through 2 θ angle of 3-25°. The results are shown in the graph of FIG. 1 in which curve A represents commercially available Mg—Al-carbonate LDH, curve B represents LDH I-6, curve C represents LDH I-1, and curve D represents LDH I-2.

It is seen from curves C and D that the peak intensity moved toward lower angle side compared to curve A suggesting enlarged interlayer spacing distance due to intercalation of magnesium acetate or cerium acetate having larger sizes. In contrast shifting of the peak intensity toward lower angle side is not seen in curve B suggesting no enlargement of interlayer spacing distance.

X-Ray Diffraction Analysis: Part 2

Figure 3:
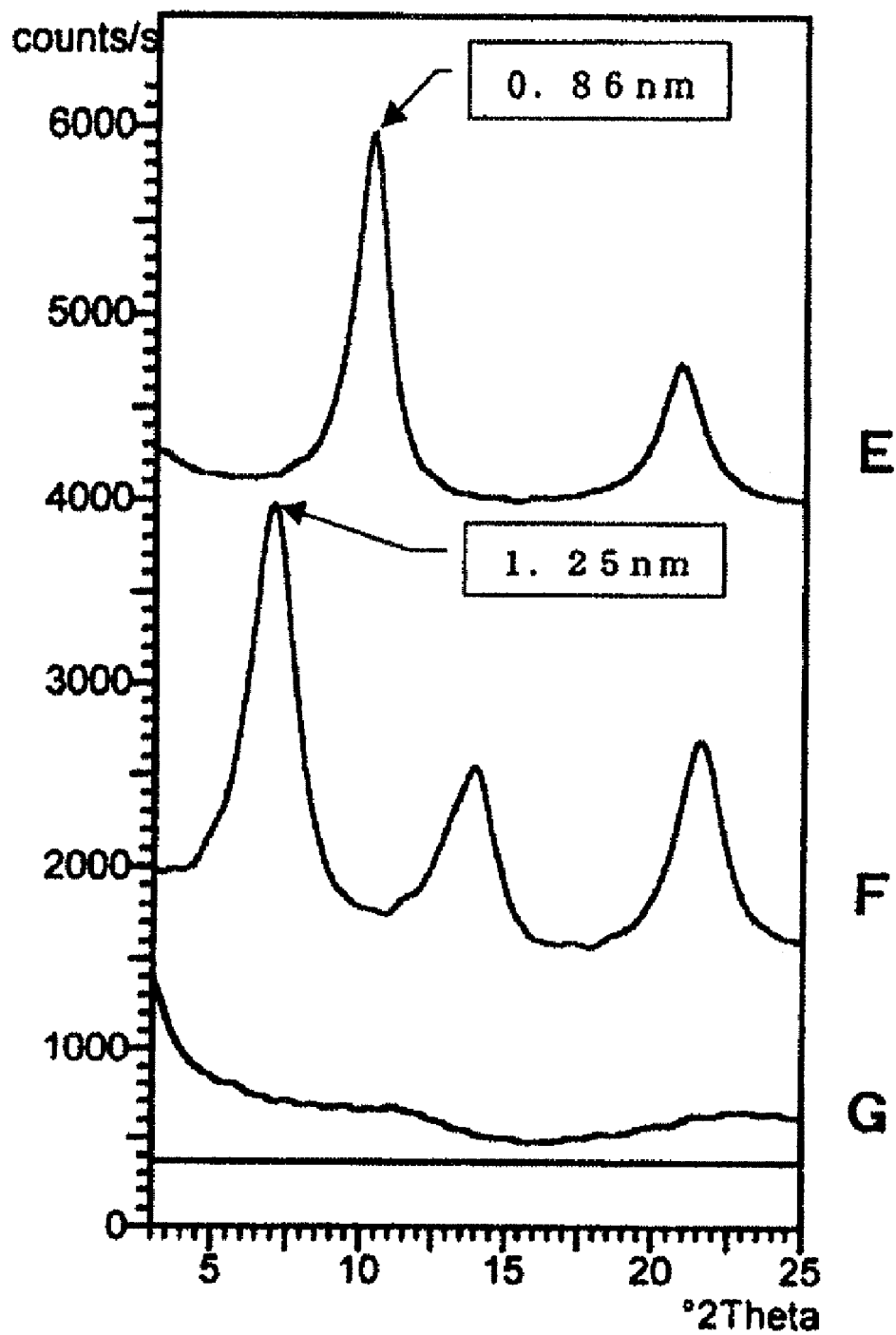
FIG. 3 shows the X-ray diffraction analysis of the LDH of the present invention when hydrated with different amounts of water.

Three samples, e.g. dry LDH I-1 containing 0% of water, LDH I-1 kneaded with 50% of water, and LDH I-1 kneaded with 70% of water were analyzed using the same instrument under the same conditions as in Part 1. The results are shown in the graph of FIG. 3 in which curve E represents dry LDH I-1, curve F represents LDH I-1 kneaded with 50% water, and curve G represents LDH I-1 kneaded with 70% water. The peak intensity moved toward lower angle side with increase in the amount of water and finally disappeared. This indicates enlarged interlayer spacing distance due to incorporation of water molecules and finally destruction of crystal structure of LDH due to delamination.

X-Ray Diffraction Analysis: Part 3

Figure 4:
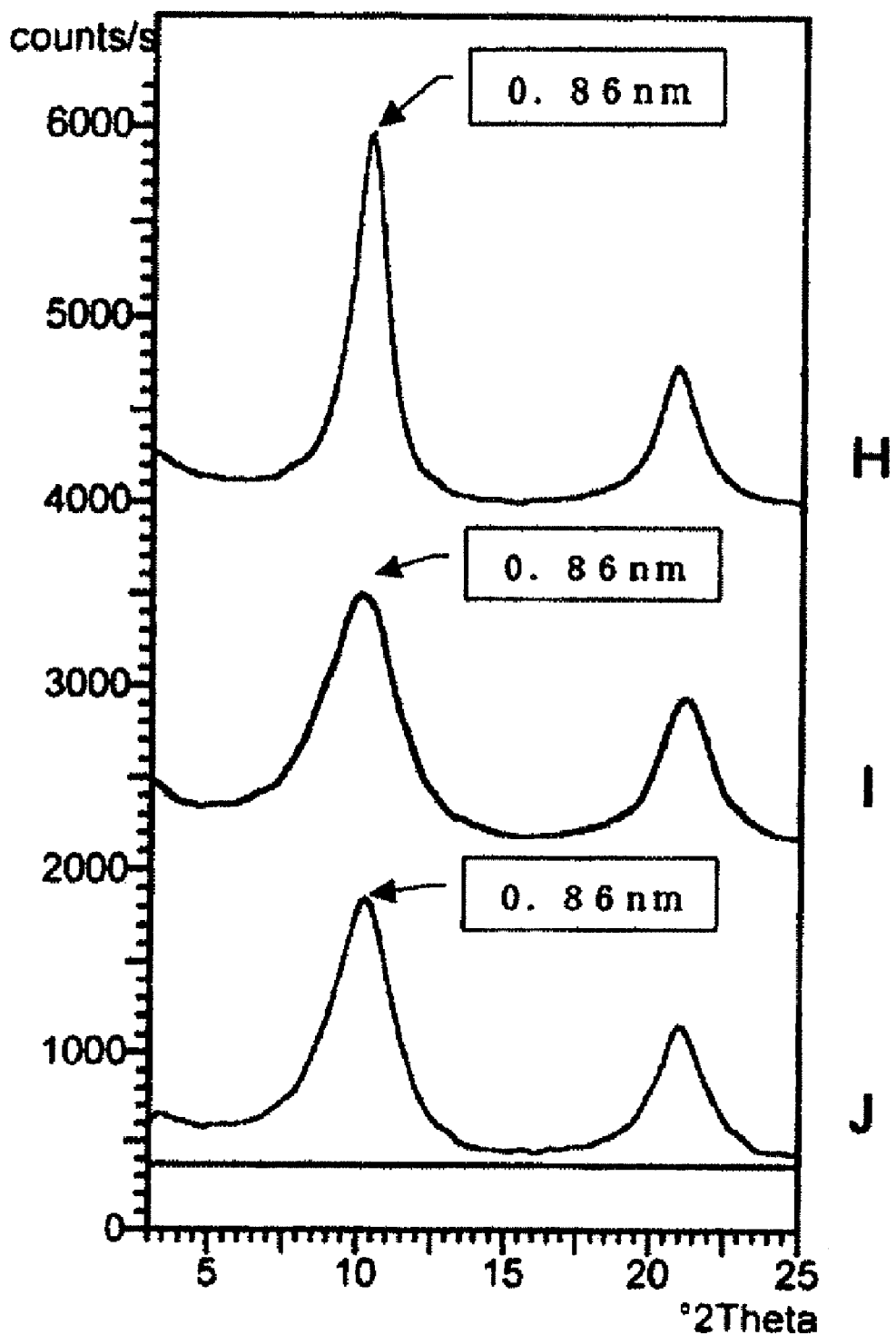
FIG. 4 shows the X-ray diffraction analysis of the LDH of the present invention after drying the hydrated LDH at 90° C. for 1 hour.
Figure 5:
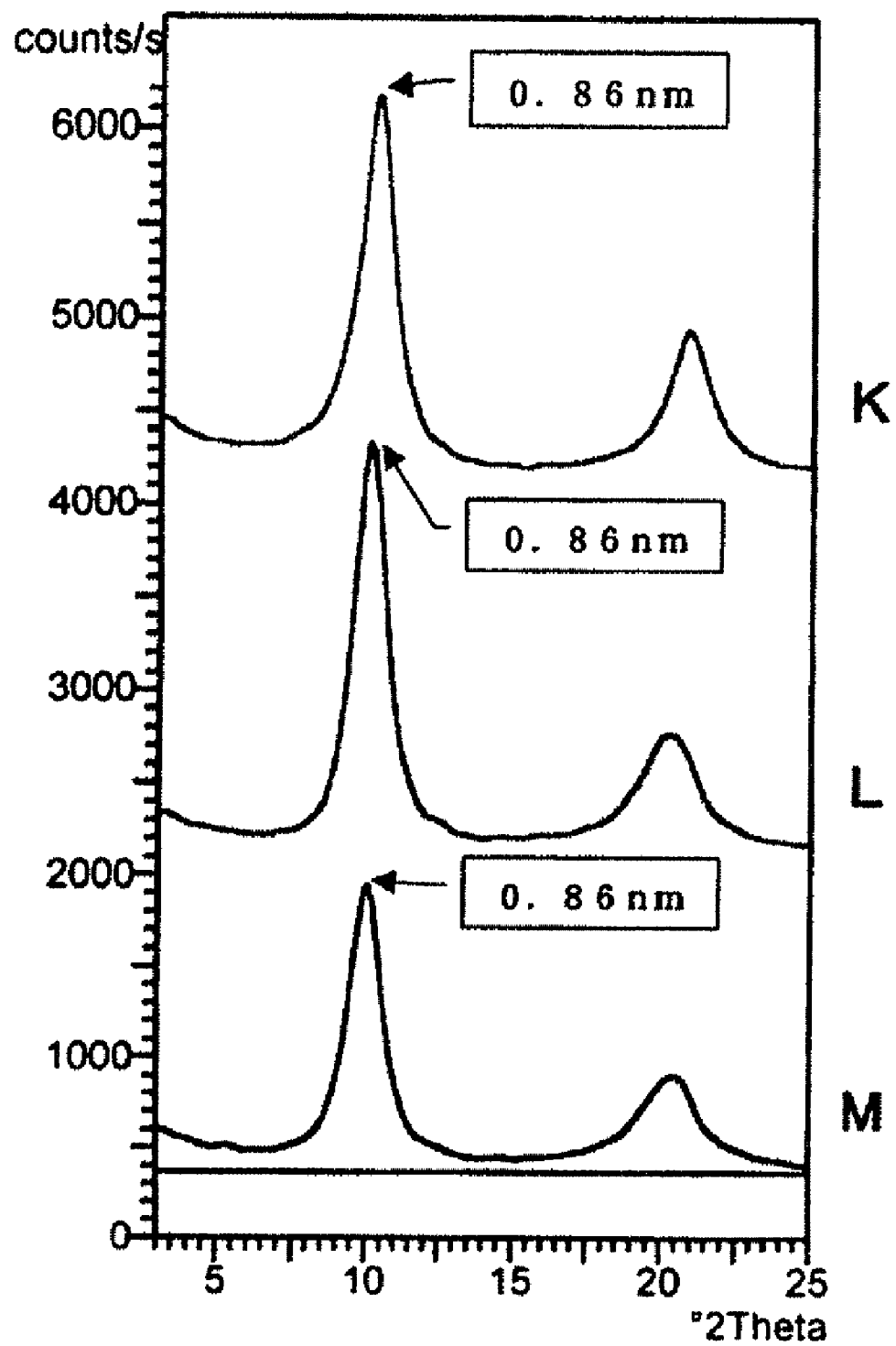
FIG. 5 shows the X-ray diffraction analysis of the LDH of the present invention after drying the hydrated LDH at 150° C. for 1 hour.

LDH I-1 kneaded with 50% water and LDH I-1 kneaded with 70% water used in Part 2 were dried at 90° C. for 1 hour and then at 150° C. for 1 hour, respectively. The dried samples were analyzed using the same instruments under the same conditions as in Part 1. FIGS. 4 and 5 show the X-ray diffraction patterns of LDH I-1 kneaded with water after drying at 90° C. for 1 hour (FIG. 4) and at 150° C. for additional 1 hour (FIG. 5), respectively. In the drawings, curves H and K represent LDH I-1 before kneading with water, curves I and L represent LDH I-1 kneaded with 50% water, and curves J and M represent LDH I-1 kneaded with 70% water. It is seen from the drawings that the LDH whose interlayer spacing distance has been enlarged or crystalline structure has been lost may return to the original state upon drying and almost the same peak intensity may be reached under strong drying conditions.

FT-IR Analysis

Figure 2:
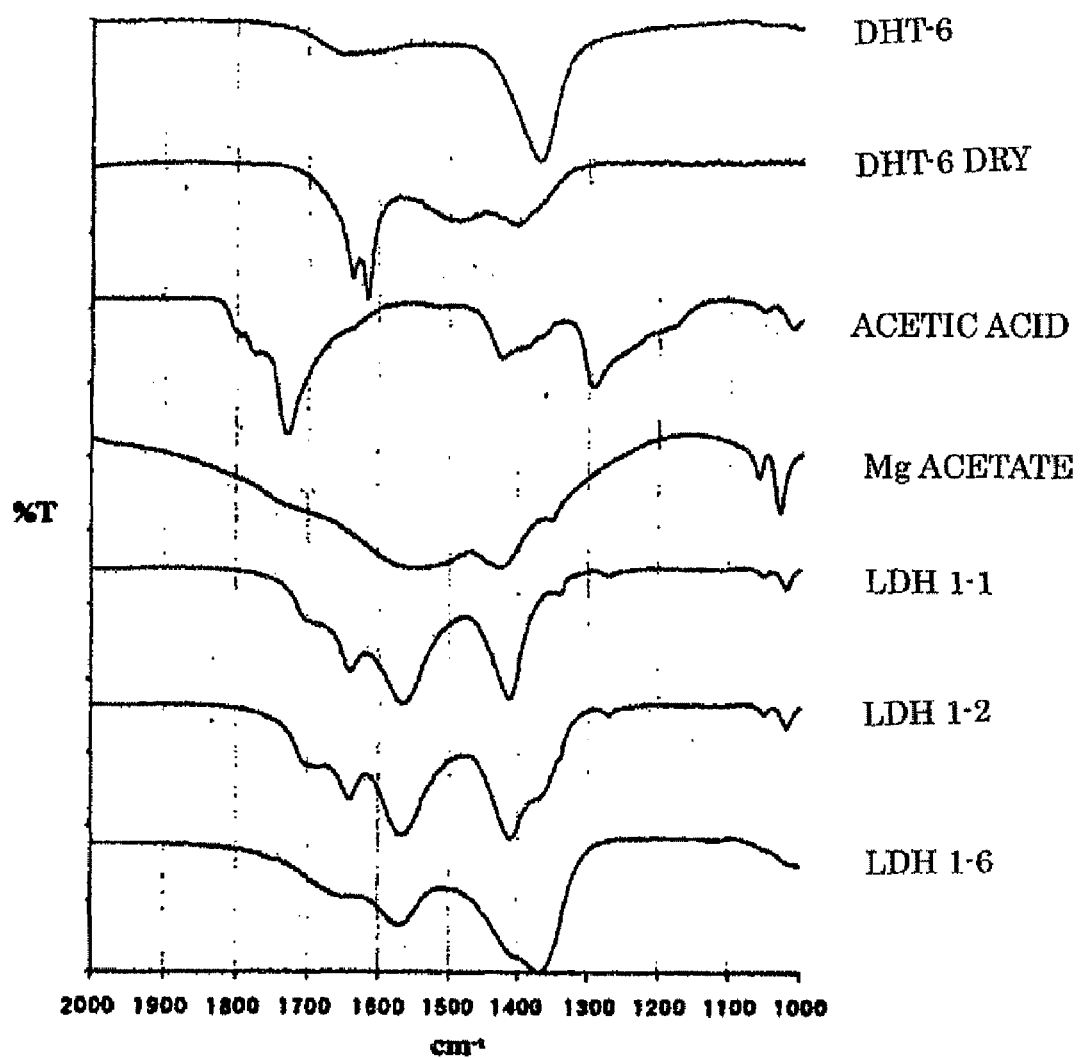
FIG. 2 shows the FT-IR analysis of the LDH of the present invention in comparison with the starting carbonate LDH, acetic acid, magnesium acetate and the corresponding sodium acetate-intercalated LDH.

FT-IR spectroscopy was carried out with respect to LDH I-1, LDH I-2 and LDH I-6 (for comparison) by the KBr tablet method using Perkin-Elmer FT-IR spectrometer. The FT-IR spectra of respective samples are shown in FIG. 2 along with the spectra of commercially available Mg—Al-carbonate LDH (DHT-6) before and after drying, acetic acid and magnesium acetate for comparison.

As seen in the drawing, the spectra of LDH I-1 and LDH I-2 substantially conform to each other but do not conform to the spectra of LDH I-6 and DHT-6. This suggests that the bivalent metal acetate of the LDH of the present invention is not intercalated as acetate ions in LDH I-6 but binds via another chemical bond.

Transmittance of Aqueous Suspension of LDH to Visible Light

Transmittance of 1% aqueous suspension of LDH 1-1 and Mg—Al carbonate LDH (DHT-6) was measured in a wavelength range between 400 nm and 780 nm. The transmittance was determined on a double beam self-recording spectrophotometer (Shimadzu Model UV-3100). The transmittance of the suspension of LDH I-1 was greater than 50% at every wavelength while the transmittance of the suspension of DHT-6 was almost 0% in the above wavelength range. These data demonstrate that the LDH of the present invention delaminates in water almost completely to give a colloidal solution while the Mg—Al carbonate LDH is dispersed in water while retaining the crystal structure.

Part III. Metal-Protecting Coating

Example III-1

Film Forming Property of Delaminated LDH

A 3% aqueous dispersion of LDH I-1 powder was applied on a glass plate using various standard bar coaters and dried at 90° C. for 48 hours. A continuous film was formed with the suspension alone. The dry film thickness and the nomination number of the standard bar coater used are shown in Table 1 below.

TABLE 1

| | Bar coater No. | | | | | | |
|---|---|---|---|---|---|---|---|
| | 8 | 16 | 26 | 36 | 46 | 55 | 65 |
| Film thickness(μm) | 0.2 | 0.4 | 0.5 | 0.9 | 1.2 | 1.4 | 1.6 |

The transmittance of each film on the glass plate prepared as above was determined in the wavelength range between 400 nm and 780 nm on a double beam self-recording spectrophotometer (Shimadzu Model 3100). The transmittance was greater than 70% in the above wavelength range for all films.

The films on the glass plate were baked in an oven at 500° C. for 1 hour and tested for the pencil hardness according to JIS K 5600-5-4. The results are shown in Table 2 below.

TABLE 2

| | Bar coater No. | | | | | |
|---|---|---|---|---|---|---|
| | 8 | 16 | 26 | 36 | 46 | 55 | 65 |
| Before baking | 4B | 4B | 4B | 5B | 5B | 5B | 5B |
| After baking | 9H | 9H | 8H | 8H | 8H | 8H | 4H |

The above results show that the film was converted to a hard scratch-resistant film by baking.

Example III-2

Metal-Protective Coating Compositions Containing Hydrosol of LDH as Vehicle

Coating compositions shown in Table 3 were prepared by dispersing the LDH of the present invention in water or a mixture of water and ethanol with or without additives. Test panels were prepared by applying the composition onto a metal substrate followed by baking. The metal substrate, coating method, baking conditions and film thickness are also shown in Table 3.

The coating compositions used in Run Nos. 1-7 are a dispersion of LDH I-1 prepared in Part I. The coating composition used in Run No. 8 is a suspension of LDH I-4 in a 7:3 mixture of water and ethanol. The coating composition used in Run No. 16 is a dispersion of LDH I-5 in water. The concentration of LDH in each composition is indicated in Table 3. The coating compositions used in Run Nos. 10-14 contain various additives in addition to LDH I-1 and their formulations are given in Table 4. The test panel of Run No. 17 (Comparative Example 1) was coated with Mg—Al carbonate LDH (DHT-6) and the test panel of Run No. 18 (Comparative Example 2) was uncoated Zinc phosphate-treated steel plate (Bonderite #144). Degreased mild steel plate SPCC-SB (JIS G 3141) and degreased galvernized steel plate SGCC were used. Electrodeposition coating was carried out at 10V for 3 minutes using stainless steel plate as counter electrode.

TABLE 3

| Run No. | LDH | Conc. Wt % | Solvent | Additive | Substrate | Coating method | Baking conditions Temp., Time | Film thickness μm |
|---|---|---|---|---|---|---|---|---|
| 1 | I-1 | 0.05 | Deion'd water | None | Mild steel | Dipping | 100° C., 10 min | 0.1> |
| 2 | I-1 | 0.1 | " | None | " | " | 200° C., 30 min | 0.1> |
| 3 | I-1 | 1.0 | " | None | " | " | 300° C., 10 min | 0.1> |
| 4 | I-1 | 5.0 | " | None | " | Bar coater | 400° C., 30 min | 0.2 |
| 5 | I-1 | 1.0 | " | None | Galv'd. steel | " | 300° C., 10 min | 0.1> |
| 6 | I-1 | 1.0 | " | None | Mild steel | Elc. Deposition | 200° C., 10 min | 0.1> |
| 7 | I-1 | 0.05 | " | None | " | Bar coater | 20° C., 24 hrs. | 0.1> |
| 8 | I-2 | 1.0 | " | None | " | " | 200° C., 20 min | 0.1> |
| 9 | I-4 | 1.0 | Deion'd.$H_2O$/ EtOH = 7:3 wt. | None | " | " | 150° C., 30 min | 0.1> |
| 10 | I-1 | 5.0 | Deion'd water | None | " | " | 400° C., 30 min | 0.2 |
| 11 | I-1 | 3.0 | Deion'd water | $TiO_2$, Zn phosphate | Zn phosphate steel (Bonde #144) | " | 200° C., 30 min | 5.3 |
| 12 | I-1 | 3.0 | " | Al tripoly phosphate | Mild steel | " | 250° C., 10 min | 4.7 |
| 13 | I-1 | 5.0 | " | μ $TiO_2$ | " | " | 200° C., 10 min | 0.3 |
| 14 | I-1 | 5.0 | " | μ ZnO | " | " | 200° C., 10 min | 0.3 |
| 15 | I-1 | 5.0 | " | $SiO_2$ sol | " | " | 200° C., 10 min | 0.2 |
| 16 | I-5 | 5.0 | " | None | " | " | 400° C., 30 min | 0.2 |
| 17 (Comp. Ex. 1) | DHT-6 | 5.0 | " | None | " | " | Not film | Not film |
| 18 (Comp. Ex 2) | — | — | — | — | Zn phosphate steel plate (Bonde #144) | — | — | 5 |

TABLE 4

| | Formulation of Coating Composition (parts as solids) | | | | |
|---|---|---|---|---|---|
| Material | No. 11 | No. 12 | No. 13 | No. 14 | No. 15 |
| LDH I-1 | 3 | 3 | 5 | 5 | 5 |
| $TiO_2$[1] | 0.3 | — | — | — | — |
| Zn phophate[2] | 1.2 | — | — | — | — |
| Al tripoly-phosphate[3] | — | 1.5 | — | — | — |
| μ $TiO_2$[4] | — | — | 2 | — | — |
| μ $ZnO$[5] | — | — | — | 2 | — |
| Silica sol[6] | — | — | — | — | — |
| Water | 100 | 100 | 100 | 100 | 10 |
| Total | 104.5 | 104.5 | 107 | 107 | 115 |

[1] Rutile $TiO_2$ JR-602, Tayca Corp.
[2] ZP-50S, Kikuchi Color Co., Ltd
[3] K-WHITE#105, Tayca Corp.
[4] $TiO_2$ microparticles MT-150W, Tayca Corp.
[5] ZnO microparticles MZ-500, Tayca Corp.
[6] SNOWTEX, Nissan Chemical Industries, Ltd. (pH9-10, $SiO_2$ content 20%)

Rust Inhibition Test

Method 1:

Specimen panels are placed in a salt spray tester maintained at an inner temperature of 35° C. and exposed to spraying solution containing 5% NaCl for 8 and 24 hours, respectively. Then the development of rust is visually examined.

Method 2:

Specimen panels are placed in a chamber maintained at a constant temperature of 20° C. and at a constant relative humidity of 80% for 24 hours. Then the development of rust is visually examined.

The degree of development of rust is judged according to the following schedules.
++: No development
+: Little development
−: Abundant development
−−: Development in full area

TABLE 5

| Run No. | LDH | Conc. Wt. % | Film thickness, μm | Method 1: Salt spray, 8 hrs. | Method 1: Salt spray, 24 hrs. | Method 2: 20° C. 80% RH, 24 hrs. |
|---|---|---|---|---|---|---|
| 1 | I-1 | 0.05 | 0.1> | − | −− | + |
| 2 | I-1 | 0.1 | 0.1> | + | − | ++ |
| 3 | I-1 | 1.0 | 0.1> | ++ | + | ++ |
| 4 | I-1 | 5.0 | 0.2 | ++ | + | ++ |
| 5 | I-1 | 1.0 | 0.1> | ++ | ++ | ++ |
| 6 | I-1 | 1.0 | 0.1> | ++ | + | ++ |
| 7 | I-1 | 0.05 | 0.1> | −− | −− | + |
| 8 | I-2 | 1.0 | 0.1> | ++ | + | ++ |
| 9 | I-4 | 1.0 | 0.1> | ++ | + | ++ |
| 10 | I-1 | 5.0 | 0.2 | ++ | ++ | ++ |
| 11 | I-1 | 10.0 | 5.3 | ++ | ++ | ++ |
| 12 | I-1 | 10.0 | 4.7 | ++ | ++ | ++ |
| 13 | I-1 | 5.0 | 0.3 | ++ | ++ | ++ |
| 14 | I-1 | 5.0 | 0.3 | ++ | ++ | ++ |
| 15 | I-1 | 5.0 | 0.2 | ++ | ++ | ++ |
| 16 | I-5 | 5.0 | 0.2 | ++ | ++ | ++ |
| 17 | DHT-6 | 5.0 | Not film | N.D. | N.D. | N.D. |
| 18 | — | — | 5 | + | + | + |

N.D.: Not determined

The test results shown in Table 5 indicate that coating films from an aqueous suspension exhibit a significant rust-inhibitory effect at a concentration of 1% or higher without any additive and a satisfactory rust-inhibitory effect at a concentration of 3% or higher when containing one or more additives. The LDH of the present invention is, therefore, useful as a vehicle of water-based rust-preventing coating composition.

Example III-3

Incorporation of LDH into Conventional Water-Based Paints

The LDH of the present invention was incorporated into conventional water-based paints containing a polymeric vehicle and applied on a metallic substrate to prepare test panels for testing rust-preventing effect.

Preparation of Test Panels

Example III-3-1

To 28.6 g of water-based epoxy ester resin dispersion (WATERSOL CD540, Dainippon Ink & Chemicals, Inc., 40% nonvolatiles) were added 2.4 g of LDH I-1, 10 g of deionized water and 140 g of 1 mm glass beads. The mixture was dispersed in a paint conditioner for 30 minutes. After adding 27.0 g of the same resin dispersion and 0.7 g of dryer (DICNATE 3110, Dainippon Ink & Chemicals, Inc.), the mixture was further dispersed in the paint conditioner for 15 minutes and then filtered through a filter paper to remove the glass beads. A paint having a PB ratio (weight ratio of pigment to resin as solids) of 0.11 was obtained. The paint was applied on degreased mild steel plate SPCC-SB (JIS G 3141) to a dry film thickness of 30 μm using a bar coater, and air dried at room temperature for 1 week to give a test panel.

Example III-3-2

Example III-3-1 was repeated except that LDH I-1 was replaced with LDH I-2.

Example III-3-3

Example III-3-1 was repeated except that LDH I-1 was replaced with LDH I-4.

Example III-3-4

Example III-3-1 was repeated except that 2.4 g of LDH I-1 was changed to a mixture of 4.4 g of LDH I-1 and 17.8 g of calcium carbonate to give a paint having a PB ratio of 1.0.

Example III-3-5

Example III-3-1 was repeated except that 2.4 g of LDH I-1 was changed to a mixture of 4.4 g of LDH I-1, 13.4 g of calcium carbonate and 4.4 g of aluminum tripolyphosphate (K-WHITE #105, Tayca Corp.) to give a paint having a PB ratio of 1.0.

Example III-3-6

Example III-3-1 was repeated except that WATERSOL CD-540 was replaced with WATERSOL CD-520 (water-soluble alkyd resin, Dainippon Ink & Chemicals, Inc., 40% nonvolatiles).

Example III-3-7

A sol was produced from 2.4 g of LDH I-1 by adding in 46 g of deionized water. The sol was dispersed with 24.9 g of acrylic resin emulsion (VONCOAT 5410, Dainippon Ink &Chemicals, Inc., 50% nonvolatiles) in a high speed dispersion mill at 3000 RPM for 5 minutes. After further addition of 20 g of VONCOAT 5410, the dispersing process was continued for additional 10 minutes. The resulting paint was applied on a mild steel plate under the same condition as Example III-3-1 and then air dried at room temperature for 1 week to give a test panel.

Example III-3-8

Cationic Electrodeposition Paint

Amine-Modified Epoxy Resin Emulsion 1900 parts of bisphenol epoxy resin having an epoxy equivalent weight of about 950 (EPON 1004, Yuka Shell Chemical) was dissolved in 1012 parts of butylcellosolve and heated to 80° C.-100° C. To the resulting solution was added dropwise 124 parts of diethylamine. The mixture was maintained at 120° C. for 2 hours to obtain a solution of amine-added epoxy resin having an amine number of 42.

Separately, 1000 parts of dimer acid polyamide resin having an amine number of 100 (VERSAMIDE 460, Henkel-Hakusui) was dissolved in 429 parts of methyl ethyl ketone and refluxed at 130-150° C. until no longer water is distilled off to ketiminize the terminal amino groups of the polyamide resin. After cooling the resulting solution was combined with the above solution of amine-added epoxy resin, heated at 100° C. for 1 hour and cooled to room temperature. A varnish of polyamide-modified amine-added epoxy resin having 68% solids was obtained. The amine number of the resin was 65.

103 parts of the varnish thus produced (70 parts as solids), 30 parts of 2-ethylhexanol-blocked tolylenediisocyanate and 15 parts of 10% acetic acid were mixed together. To the mixture was added dropwise 150 parts of deionized water over 15 minutes with vigorous stirring to obtain an emulsion having 34% solids.

Pigment Paste 5 parts of the modified epoxy resin varnish produced above having 68% solids, 2.6 parts of 10% acetic acid, 17 parts of $TiO_2$ pigment, 8 parts of clay, 0.3 parts of carbon black, 2 parts of diocyl tin oxide, and 5 parts of LDH I-1 were mixed together. The mixture was diluted to 50% solids with deionized water and then milled in a ball mill to a particle size less than 10 μm for 40 minutes to obtain pigment paste.

Electrodeposition Paint and Coating

An electrodeposition paint was produced by blending 315 parts of the above emulsion, 80 parts of the above pigment paste and an amount of deionized water sufficient to give 20% solid. The resulting paint was applied electrically on zinc phosphate-treated steel plate (Bonderite #144) as cathode at 250V to a dry film thickness of 20 μm, washed with water and baked at 160° C. for 30 minutes to prepare a test panel.

Example III-3-9

Example III-3-1 was repeated except that the substrate was changed to zinc phosphate-treated steel plate (Bonderite #144).

Comparative Example III-3-1

Example III-3-1 was repeated except that LDH I-1 was dispensed with.

Comparative Example III-3-2

Example III-3-1 was repeated except that LDH I-1 was replaced with calcium carbonate.

Comparative Example III-3-3

Example III-3-1 was repeated except that LDH I-1 was replaced with Mg—Al carbonate LDH (DHT-6).

Comparative Example III-3-4

Example III-3-1 was repeated except that LDH I-1 was replaced with talc (Talc SSS, Nippon Talc Co., Ltd.)

Comparative Example III-3-5

Example III-3-8 was repeated except that LDH I-1 in the pigment paste was replaced with calcium carbonate.

Comparative Example III-3-6

Example III-3-9 was repeated except that LDH I-1 was dispensed with.

Salt Spray Test

Test panels of Examples and Comparative Examples were given crosscut marking with knife on the coated surface and exposed to spraying 5% NaCl solution for a prescribed time. Development of rust on planar surfaces and the width of corrosion extending from the cut edge were visually examined. the rust inhibitory effect of paints containing LDH or other additives are judged according to the following schedule.

1. Planar portion:
    ++: Almost no development of blister and rust
    +: Little development of blister and rust
    −: Abundant development of blister and rust
    −−: Development of blister and rust in all area
2. Cut portion
    ++: Corrosion width <0.5 mm
    +: Corrosion width 0.5-1 mm
    −: Corrosion width 1-3 mm
    −−: Corrosion width >3 mm The results are shown in Table 6.

TABLE 6

| EX. No. | Resin | Pigment | Substrate | Salt spray test time, hrs. | Planar portion | Cut portion |
|---|---|---|---|---|---|---|
| EX. III-3-1 | CD540 | LDH I-1 | SPCC | 240 | ++ | + |
| EX. III-3-2 | CD540 | LDH I-2 | SPCC | 240 | ++ | + |
| EX. III-3-3 | CD540 | LDH I-4 | SPCC | 240 | ++ | + |
| EX. III-3-4 | CD540 | LDH I-1, $CaCO_3$ | SPCC | 240 | ++ | ++ |
| EX. III-3-5 | CD540 | LDH I-1, #105, $CaCO_3$ | SPCC | 240 | ++ | ++ |
| EX. III-3-6 | CD520 | LDH I-1 | SPCC | 240 | ++ | + |
| EX. III-3-7 | Boncoat 5410 | LDH I-1 | SPCC | 240 | ++ | ++ |
| EX. III-3-8 | ED resin | LDH I-1 | Bonde #144 | 480 | ++ | ++ |
| EX. III-3-9 | CD540 | LDH I-1 | Bonde #144 | 24 | + | + |
| Com. III-3-1 | CD540 | — | SPCC | 240 | − | −− |
| Com. III-3-2 | CD540 | $CaCO_3$ | SPCC | 240 | − | −− |

TABLE 6-continued

| EX. No. | Resin | Pigment | Substrate | Salt spray test time, hrs. | Planar portion | Cut portion |
|---|---|---|---|---|---|---|
| Com. III-3-3 | CD540 | DHT-6 | SPCC | 240 | − | -- |
| Com. III-3-4 | CD540 | Talc | SPCC | 240 | − | -- |
| Com. III-3-5 | ED resin | $CaCO_3$ | Bonde #144 | 480 | + | -- |
| Com. III-3-6 | CD540 | — | Bonde #144 | 24 | -- | -- |

Examples and Comparative Examples in Table 6 demonstrate that the LDH of the present invention is useful as a rust-inhibiting pigment to be formulated in conventional water-based paints whereas LDH having intercalated carbonic acid is not effective for the prevention of rust development.

Part IV. Additive to Cosmetic Preparations

The LDH of the present invention delaminates in water to form a colloid solution or sol. Thus the LDH may be incorporated in a variety of skin-care cosmetic preparations such as creams, lotions, milks or foundations as a stabilizing thickening agent or humectant. Exemplifying formulations are given below.

| Material | wt. parts |
|---|---|
| Lotion: | |
| L-arginine | 1.5 |
| Sodium citrate | 0.05 |
| Preservative | 0.2 |
| 1,3-Butylene glycol | 3.0 |
| Glycyrrlizin dipotassium | 0.1 |
| Sodium pyrrolidone carboxylate | 2.0 |
| Citric acid | q.v |
| Perfume | 0.05 |
| LDH I-1 | 2.0 |
| Purified water | q.s. |
| Total | 100 |
| Milk: | |
| Stearic acid | 0.2 |
| Cetyl alcohol | 1.5 |
| Vaseline | 6.0 |
| Squalane | 6.0 |
| Glycerol | 2.0 |
| 2-Ethylhexanate ester | 0.5 |
| Sorbitan monooleate | 2.0 |
| Dipropylene glycol | 2.0 |
| Triethanolamine | 1.0 |
| Perfume | 0.1 |
| LDH I-1 | 0.1 |
| Purified water | 78.6 |
| Total | 100 |
| Varnishing cream: | |
| Stearic acid | 7.5 |
| Stearyl alcohol | 4.0 |
| Butyl stearate | 5.5 |
| Ethyl p-hydroxybenzoate | 0.5 |
| Perfume | 0.1 |
| LDH I-1 | 0.2 |
| Purified water | 73.8 |
| Total | 100 |
| Foundation: | |
| Talc | 20.5 |
| Mica | 34.5 |
| Kaoline | 5.5 |

-continued

| Material | wt. parts |
|---|---|
| $TiO_2$ | 10.0 |
| Brilliant pigment ($TiO_2$ coated mica) | 3.0 |
| Zinc stearate | 1.0 |
| Yellow iron oxide | 2.8 |
| Black iron oxide | 0.2 |
| Nylon powder | 10.0 |
| Squalane | 6.0 |
| Octyl dodecyl myristate | 2.0 |
| Vaseline | 2.5 |
| Ethyl p-hydroxy benzoate | 0.5 |
| Perfume | 0.1 |
| LDH I-1 | 0.5 |
| Total | 100 |

The invention claimed is:

1. A layered double hydroxide comprising:
a plurality of basal layers of a double hydroxide of Formula (I):

$$M(II)_{1-x}M(III)_x(OH)_2 \quad (I)$$

wherein M(II) is Mg, M(III) is Al, and x is 0.2 to 0.33, and a plurality of intercalation layers between each of the adjacent basal layers comprising (a) Mg acetate, and (b) water of intercalation,
said layered double hydroxide being produced by a process comprising calcining a carbonate-type layered double hydroxide of Formula (II):

$$[M(II)^{2+}_{1-x}M(III)^{3+}_x(OH)_2][(CO_3)_{x/2} \cdot yH_2O] \quad (II)$$

wherein y is a real number greater than zero;
reacting the calcined product with an aqueous solution of Mg acetate;
separating the resulting solid product from the solution; and
drying and pulverizing the separated solid product.

2. A process for producing the layered double hydroxide of claim 1 comprising:
calcining a carbonate-type layered double hydroxide of Formula (II):

$$[M(II)^{2+}_{1-x}M(III)^{3+}_x(OH)_2][(CO_3)_{x/2} \cdot yH_2O] \quad (II)$$

wherein MOD, M(III) and x are as defined in claim 1, and y is a real number greater than zero;
reacting the calcined product with an aqueous solution of Mg acetate;
separating the resulting solid product from the solution; and drying and pulverizing the separated solid product.

3. The process according to claim 2 wherein said carbonate-type layered double hydroxide is calcined at a temperature between 400° C. and 800° C.

4. The process according to claim 2 wherein at least equimolar amount of said acetate salt is reacted with said calcined product calculated as $Al_2O_3$.

5. A metal-protective coating composition comprising the layered double hydroxide of claim 1 as a film forming material.

6. The metal protective coating composition of claim 5 further comprising a pigment.

7. A method of forming a scratch resistant film on a metallic substrate comprising applying the coating composition of claim 5 on said substrate to form a film, and baking the film at a temperature above 350° C.

8. A metal-protective coating composition comprising an aqueous solution, emulsion or dispersion of a water-based vehicle resin and the layered double hydroxide of claim 1 dispersed in said solution, emulsion or dispersion.

9. The metal coating composition of claim 8 wherein said vehicle resin is an air drying resin.

10. The metal coating composition of claim 8 wherein said vehicle resin is a thermosetting resin.

11. A cosmetic preparation comprising an amount of the layered double hydroxide of claim 1 effective for stabilization or humectation of said cosmetic preparation.

12. The cosmetic preparation of claim 11 in the form of lotions, milks, creams or foundations.

13. The layered double hydroxide of claim 1 wherein the interlayer spacing distance between each of the adjacent basal layers is enlarged compared with that of the carbonate-type layered double hydroxide of Formula (II) upon X-ray diffraction analysis.

* * * * *